United States Patent [19]

Sezaki et al.

[11] 4,156,719
[45] May 29, 1979

[54] COMPOSITIONS FOR RECTAL USE

[75] Inventors: Hitoshi Sezaki; Shozo Muranishi, both of Kyoto, Japan

[73] Assignee: Yamanouchi Pharmaceutical Co., Ltd., Tokyo, Japan

[21] Appl. No.: 880,603

[22] Filed: Feb. 23, 1978

[30] Foreign Application Priority Data

Feb. 28, 1977 [JP] Japan .................. 52-21720

[51] Int. Cl.² .................. A61K 35/00; A61K 37/00
[52] U.S. Cl. .................. 424/118; 424/177; 424/181; 424/183; 424/246
[58] Field of Search .................. 424/177, 365

[56] References Cited

U.S. PATENT DOCUMENTS

| | | | |
|---|---|---|---|
| Re. 28,819 | 5/1976 | Thompson | 424/177 |
| 1,904,257 | 4/1933 | Stoll et al. | 424/177 |
| 2,472,640 | 6/1949 | Wilcox et al. | 424/177 |
| 2,865,859 | 12/1958 | Lubowe | 424/177 |
| 3,089,818 | 5/1963 | Stone | 424/177 |
| 3,219,529 | 11/1965 | Nash et al. | 424/365 |
| 3,220,923 | 11/1965 | Scholtan | 424/365 |
| 3,384,544 | 5/1968 | Walton et al. | 424/365 |
| 4,005,190 | 1/1977 | Mader et al. | 424/365 |

OTHER PUBLICATIONS

T. R. Bates, Dissertation Abst. 1966, pp. 2004B–2005B.
P. Samuel, et al., Chem. Abst. 70, (1969) 1497z.
N. Nishimura, et al., Chem. Abst. 69 (1968) 167j.
A. Thakkar, Chem. Abst. 73 (1970) 123482y.
W. J. Simmonds, Chem. Abst. 77 (1972) 148689s.
L. Mitterhauszerova, et al., Chem. Abst. 81, 1974 17263h.

Primary Examiner—Delbert R. Phillips
Attorney, Agent, or Firm—Burgess, Ryan and Wayne

[57] ABSTRACT

A micellar solution composition for rectal use comprising (a) a water-soluble drug which is poorly absorbable on oral administration (b) a middle-higher fatty acid and/or the mono- or di-glyceride thereof, (c) a bile acid and/or a nonionic surface active agent, and (d) water; and a powder composition for rectal use prepared by drying the aforesaid micellar solution composition.

13 Claims, No Drawings

COMPOSITIONS FOR RECTAL USE

DETAILED DESCRIPTION OF THE INVENTION

The present invention relates to a composition for rectal use of a water-soluble drug which is poorly absorbable on oral administration. More particularly, the invention relates to a micellar solution composition comprising (a) a water-soluble drug which is poorly absorbable on oral administration, (b) a middle-higher fatty acid and/or a mono- or di-glyceride thereof, (c) a bile acid and/or a nonionic surface active agent, and (d) water; and also a powder composition for rectal use prepared by drying the micellar solution composition with, if desired, the addition of other pharmaceutically acceptable ingredients. The invention relates further to the processes of producing these compositions.

The compositions for rectal use provided by the present invention include a micellar solution type composition and a powder type composition, and the both compositions have the unusual feature in that water-soluble drugs which are poorly adsorbable on oral administration can be effectively absorbed on rectal administration without being accompanied by damage of the rectal epithelium.

A dosage form of so-called poorly absorbable drugs, that is water-soluble drugs which are poorly absorbable on oral administration is at present, limited to an injection form for intravenous administration and intramuscular administration. However, the administration by injection is troublesome for patients and is painful as well as having harmful after-effects such as muscle injuries upon injection, etc. There are known formulations for rectal use prepared by dispersing in suppository bases and nonionic surface active agents poorly absorbable drugs such as carbenicillin, sulbenicillin, cephazolin, cephaloridine, cephalothin, etc., as disclosed in U.S. Pat. No. 3,881,012 and Japanese Patent Application Laid Open No. 30,519/1974. However, some of these formulations for rectal use are insufficient in absorption and some of them cause damage of the rectal epithelium, and hence formulations for rectal use containing the poorly absorbable drugs which can be practically used have not yet been obtained.

Thus, as the result of various investigations on compositions for rectal use which can let the poorly absorbable drugs be absorbed without being accompanied by damage of the rectal epithelium, the inventors have discovered that the micellar solution composition prepared by compounding a poorly absorbable drug with a fatty acid and/or the mono- or di-glyceride thereof, a bile acid and or a nonionic surface active agent, and water or the powder composition obtained by drying the micellar solution composition with, if desired, the addition of other conventional pharmaceutical ingredients is suitable as the composition for rectal use.

Since the absorption accelerating effect of poorly absorbable drugs by the composition of this invention is particularly remarkable in the colon and the rectum, the compositions of this invention are particularly suitable for rectal use.

The micellar solution in this invention is a visually transparent or semitransparent solution in which a micelle or mixed micelle is formed. Even if the aforesaid components (a), (b), (c) and (d) constituting the composition of this invention are merely mixed, a micelle or mixed micelle is not formed but a simple emulsion or suspension is formed. The technique of producing a micellar solution, that is a visually transparent or semitransparent solution having formed therein a micelle or mixed micelle is a conventional one for persons skilled in the art but it has not been reported to apply such a micellar solution for rectal use. It is unexpected that when a poorly absorbable drug is administered via the rectum as the micellar solution thereof according to this invention, the poorly absorbable drug can be effectively absorbed in the body through the colon and the rectum without being accompanied by damage to the rectal epithelium. The fact that the micellar solution of this invention is administered to the rectum without being accompanied by damage of the rectal epithelium has been confirmed by microscopic studies of the rectal epithelium of rats.

The powder composition of this invention is the composition obtained by drying the above-mentioned micellar solution as it is or with the addition of conventional pharmaceutical ingredients such as mannitol, etc., and when the powder compositions is dispersed in water, the state of micelle or mixed micelle is immediately reproduced to provide a visually transparent or semitransparent solution.

It has not yet been reported to apply a powder composition prepared by drying a micellar solution. It is unexpected that when a poorly absorbable drug is administered to the rectum as the powder composition prepared by drying the micelle solution, the poorly absorbable drug can be effectively absorbed in the body through the colon and the rectum without being accompanied by damage to the rectal epithelium as in the case of using the micellar solution composition of this invention.

The reason why a poorly absorbable drug is effectively absorbed in the body from the colon or the rectum by administering it as the micellar solution or the powder composition for rectal use according to this invention is considered to be that in the composition of this invention, the poorly absorbable drug is captured by a micelle or mixed micelle and with the absorption of the fatty acid and/or the mono- or di-glyceride thereof constituting the micelle or mixed micelle into the body, the absorption of the drug is remarkably accelerated. In addition, it is considered that the bile acid and/or the surface active agent constituting the micelle or the mixed micelle is not absorbed in the body and does not directly contribute to the acceleration of the absorption of the poorly absorbable drug.

Now, the poorly absorbable drugs used in this invention are water-soluble drugs which are sparingly soluble in water on oral administration or show insufficient medical effect by oral use and as such poorly absorbable drugs, there are polysaccharides or polysaccharide type antitumour materials and the salts thereof such as heparin, zymosan, lentinan, Krestin (PS-K), etc.; peptide type antitumour materials such as neocarzinostatin, bleomycin, etc.; peptides, proteins, or enzymes such as tetragastrin, insulin, blomelain, etc.; aminoglycoside group antibiotics such as Kanamycins, Gentamycins, Streptomycins, Fradiomycins, Ribostamycins, Sisomicins, etc.; penicillin series antibiotics and the sodium salts thereof such as benzylpenicillin, carbenicillin, sulbenicillin, piperacillin, etc.; and cephalosporin C series antibiotics and the sodium salts thereof such as cefazolin, cephaloglycin, caphalothin, cephaloridine, etc.

Also, the middle-higher fatty acids used in this invention are fatty acids having 6–18 carbon atoms and practical examples of them are straight chain saturated fatty acids such as caprylic acid, lauric acid, stearic acid, etc.; branched chain saturated fatty acids such as 2-butyl-5-methylpentanoic acid, 3-methylpentadecanoic acid, etc.; unsaturated fatty acids such as 4-hexenoic acid, oleic acid, 2,5-dimethyl-2-heptadecenoic acid, linolic acid, linoleic acid, arachidonic acid, etc.; and the sodium salts and potassium salts of these fatty acids.

The middle-higher fatty acid mono-glycerides used in this invention are the esters of the aforesaid middle-higher fatty acids and glycerol and examples of them are 1-monoolein, 2-monopalmitin, etc. Furthermore, one of the remaining two hydroxyl groups of the mono-glycerides may further form an ester bond with choline phosphate and examples of such mono-glycerides are lypolecithin, etc. The fatty acid di-glycerides used in this invention are the glycerin esters of the aforesaid middle-higher fatty acids or the glyceririn esters of the aforesaid middle-higher fatty acids and other lower fatty acids and there are monoacid group type fatty acid glycerides such as 1,3-dilinolein, 1,2-distearin, etc., and mixed acid group type fatty acid diglycerides such as 1-aceto-3-olein, 1-lauro-2-olein, 1-palmito-2-olein, etc.

Furthermore, typical examples of the nonionic surface active agents used in this invention are polyoxyethylene sorbitan fatty acid esters (e. g., Polysorbate 80, Tween 80, a registered trade mark, made by Kao Atlas Co.), polyoxyethylene fatty acid esters (e. g., Polyoxyl stearate 40, Nikkol MYS-40, a registered trade mark, made by Nikko Chemicals Co.), polyoxyethylene hardened castor oil derivatives (e. g., Nikkol HCO-60, a registered trade mark, made by Nikko Chemicals Co.), sorbitan fatty acid esters (e. g., Nikkol SO-10, a registered trade mark, made by Nikko Chemicals Co.), copolymers of polypropylene glycol and polyethylene glycol (e. g., Pluronic F68, a registered trade mark, made by Asahi Denka K. K.), and saccharose fatty acid esters (e. g., Ryoto Sugar Ester P1570, a registered trade mark, made by Ryoto K. K.).

Examples of the bile acids used in this invention are cholic acid, taurocholic acid, glycocholic acid, deoxycholic acid, taurodeoxycholic acid, glycodeoxycholic acid, chenodeoxycholic acid, taurochenodeoxycholic acid, glycochenodeoxycholic acid, the sodium salts and potassium salts of these cholic acids, and the like.

The aforesaid nonionic surface agents and the bile acids may be used solely or as a proper combination of them.

Moreover, water used in this invention may be water alone or may be an aqueous buffer solution, an aqueous diluted acid solution or an aqueous diluted alkali solution.

For producing the micellar solution composition for rectal use of this invention, the fatty acid and/or the mono- or diglyceride thereof is added to an aqueous solution containing the poorly absorbable drug and the nonionic surface active agent and/or the bile acid and the mixture is stirred vigorously. In this case, when the fatty acid or the mono- or di-glyceride of fatty acid which is in a solid state at room temperature is used, it is added after it is first melted. Also, the stirring is continued by means of sonification, homogenization, etc., until a visually transparent or semitransparent solution is formed to provide the micellar solution composition.

The preferred compounding ratio of each component is properly controlled according to the kind of the poorly absorbable drug. For example, when insulin is used as the poorly absorbable drug, it is preferred that the solution contains 2,500–200,000 units of insulin, 5–100 millimoles of the fatty acid and/or the mono- or di-glyceride thereof, and 0.3–60 g. of the bile acid and/or the nonionic surface active agent per liter of the solution; when a polysaccharide such as heparin is used as the poorly absorbable drug, it is preferred that the solution contains 50,000–10,000,000 units of the drug, 5–100 millimoles of the fatty acid and/or the mono- or di-glyceride thereof, and 0.3–60 g. of the bile acid and/or the nonionic surface active agent per liter of the solution; when an aminoglycoxide group antibiotic such as Gentamycin is used as the poorly absorbable drug, it is preferred that the solution contains 1–100 g. of the drug, 5–100 millimoles of the fatty acid and/or the mono- or di-glyceride thereof, and 0.3–60 g. of the bile acid and/or the nonionic surface active agent per liter of the solution; and when a penicillin series or cephalosporin series antibiotic such as benzylpenicillin, cephalothin, etc., is used as the poorly absorbable drug, it is preferred that the solution contains 25–250 g. of the drug, 5–100 millimoles of the fatty acid and/or the mono- or di-glyceride thereof, and 0.3–60 g. of the bile acid and/or the nonionic surface active agent per liter of the solution.

Thus, the micellar solution composition for rectal use having formed therein a micelle or mixed micelle. By "micelle or mixed micelle" in this invention is meant the micelle or the mixed micelle formed by the aforesaid bile acid and/or the nonionic surface active agent.

Then, by drying the micellar solution composition thus obtained as it is or, if desired, with the addition of infredients for pharmaceutics such as mannitol, a powder composition for rectal use is obtained. The drying step is usually performed by lyophilization or spray drying.

The composition for rectal use of this invention is administered as it is or with the addition of a stabilizer, an antiseptic, a diluent, etc. The micellar solution composition may be used as a form which is administered using an injector, etc., for rectal use. Also, the powder composition of this invention may be used as soft capsules for rectal use by filling in soft capsules, or as rectal suppositories by dispersing it in an ordinary suppository base followed by molding by a conventional manner, or further as rectal suppositories by adding thereto other pharmaceutical ingredients followed by compression molding.

Then, the invention will further be explained in more detail by referring to the experiments showing the absorbability of the poorly absorbable drugs in the compositions for rectal use of this invention and the examples showing the production of the compositions for rectal use of this invention.

EXPERIMENT 1

The micellar solution of this invention prepared by adding the fatty acid and/or the mono- or di-glyceride thereof to a phosphoric acid buffer solution (pH 6.5) containing the bile acid and/or the nonionic surface active agent together with streptomycin, cefazolin, or Gentamycin with stirring by sonification; a phosphoric acid buffer solution (pH 6.5) (control sample) containing streptomycin, cefazolin, or Gentamycin; or a solution (control sample) prepared by further adding to the phosphoric acid buffer solution shown above the bile acid and/or the nonionic surface active agent with stirring, and the composition was administered to the rectum of rats and after one hour since the administration, the concentrations of the drugs in blood were measured for comparison. The administration to the rats was performed as follows; that is, 20 mg/10ml./kg. of streptomycin or 10 mg./10 ml./kg. of cefazolin or Gentamycin was administered to male Wister rats weighing 200-250 g. fasted for 24 hours just before the experiment at the rectal portion as the loop of large intestine. The concentration of the drug in blood after one hour following the administration was measured by a biological verification method. The results are shown in Table I.

Table I

| Test sample | Formulation | | | Concentration in blood (μg/ml) |
|---|---|---|---|---|
| Example 1 (Micellar soln.) | Streptomycin | 2.0 | g/l. | 8.0 |
| | Sodium glycocholate | 4.9 | g/l. | |
| | Oleic acid | 10 | mM/l. | |
| Control | Streptomycin | 2.0 | g/l. | <1.5 |
| | Sodium glycocholate | 4.9 | g/l. | |
| Example 12 (Micellar soln.) | Streptomycin | 2.0 | g/l. | 13.4 |
| | Sodium taurocholate | 5.4 | g/l. | |
| | Oleic acid | 10 | mM/l. | |
| Example 13 (Micellar soln.) | Streptomycin | 2.0 | g/l. | 16.0 |
| | Sodium taurocholate | 5.4 | g/l. | |
| | Linoleic acid | 10 | mM/l. | |
| Example 14 (Micellar soln.) | Streptomycin | 2.0 | g/l. | 24.2 |
| | Sodium taurocholate | 5.4 | g/l. | |
| | Lysolecithin | 10 | mM/l. | |
| Example 15 (Micellar soln.) | Streptomycin | 2.0 | g/l. | 11.0 |
| | Sodium taurocholate | 5.4 | g/l. | |
| | 1-Monoolein | 10 | mM/l. | |
| Control | Streptomycin | 2.0 | g/l. | <1.5 |
| | Sodium taurocholate | 5.4 | g/l. | |
| Control | Streptomycin | 2.0 | g/l. | <1.5 |
| Example 2 (Micellar soln.) | Gentamycin | 1.0 | g/l. | 6.9 |
| | Sodium glycocholate | 4.9 | g/l. | |
| | 1-Monoolein | | | |
| Control | Gentamycin | 1.0 | g/l. | <0.6 |
| | Sodium glycocholate | 4.9 | g/l. | |
| Control | Gentamycin | 1.0 | g/l. | <0.6 |
| Example 16 (Micellar soln.) | Cefazolin | 1.0 | g/l. | 2.3 |
| | Sodium taurocholate | 5.4 | g/l. | |
| | 1-Monoolein | 10 | mM/l. | |
| Control | Cefazolin | 1.0 | g/l. | 0.3 |
| | Sodium taurocholate | 5.4 | g/l. | |
| Contol | Cefazolin | 1.0 | g/l. | 0.2 |

EXPERIMENT 2

The micellar solution of this invention prepared by adding the fatty acid and/or the mono-glyceride thereof to an aqueous solution containing heparin sodium and a bile acid and/or the nonionic surface active agent, with stirring by sonification; an aqueous solution (control) containing heparin sodium; or a solution (control prepared by adding further a bile acid and/or the nonionic surface active agent to the above aqueous solution was administered to the recta of rats and the heparin activity in blood after 30 minutes since the administration thereof was measured for comparison. The administration to the rats was same as in Experiment 1. The doses of heparin sodium were 760 unit/10 ml./kg. The heparin activity in blood was expressed as the plasma clearing activity by the reduction extent of turbidity at 650 mμ.

The results are shown in Table II.

Table II

| Test sample | Formulation | | | Heparin activity in blood 30 min. |
|---|---|---|---|---|
| Example 3 (Micellar soln.) | Heparin sodium | 760 | unit/l. | 0.298 |
| | Sodium taurocholate | 5.4 | g/l. | |
| | Oeic acid | 10 | mM/l. | |
| Example 4 (Micellar soln.) | Heparin sodium | 760 | unit/l. | 0.310 |
| | Sodium taurocholate | 5.4 | g/l. | |
| | 1-Monoolein | 10 | mM/l. | |
| Control | Heparin sodium | 760 | unit/l. | 0.046 |
| | Sodium taurocholate | 5.4 | g/l. | |
| Example 5 (Micellar soln.) | Heparin sodium | 760 | unit/l. | 0.380 |
| | Polysorbate 80 | 2.0 | g/l. | |
| | Oleic acid | 10 | mM/l. | |
| Control | Heparin sodium | 760 | unit/l. | 0.043 |
| | Polysorbate 80 | 2.0 | g/l. | |
| Example 6 (Micellar soln.) | Heparin sodium | 760 | unit/l. | 0.334 |
| | Nikkol HCO-60 | 2.0 | g/l. | |
| | Oleic acid | 10 | mM/l. | |
| Control | Heparin sodium | 760 | unit/l. | 0.039 |
| | Nikkol HCO-60 | 2.0 | g/l. | |
| Control | Heparin sodium | 760 | unit/l. | 0.025 |

EXPERIMENT 3

The micellar solution of this invention prepared by adding the fatty acid and/or the monoglyceride thereof to an aqueous solution containing bleomycin and a bile acid and/or the nonionic surface active agent with stirring by sonification or an aqueous solution (control) containing bleomycin was administered to the rectum of rats and thereafter, the concentration in blood was measured for comparison. The administration procedure was the same as in Experiment 1. The doses of bleomycin were 25 mg./10 ml./kg. The concentration in blood was measured by a biological verification method. The results are shown in Table III.

Table III

| Test sample | Formulation | | |
|---|---|---|---|
| Example 17 (Micellar solution) | Bleomycin | 2.5 | g./liter |
| | Sodium taurocholate | 5.4 | g./liter |
| | 1-Monolein | 10 | mM/liter |
| Example 18 (Micellar solution) | Bleomycin | 2.5 | g./liter |
| | Nikkol HCO-60 | 2.0 | g./liter |
| | Oleic acid | 10 | mM/liter |
| Control | Bleomycin | 2.5 | g./liter |

| | Concentration in plasma (μg./ml.) | | | | |
|---|---|---|---|---|---|
| Test sample | 5 min. | 15 min. | 30 min. | 45 min. | 60 min. |
| Example 17 | 10.1 | 21.5 | 25.9 | 21.4 | 13.8 |
| Example 18 | 6.8 | 16.0 | 19.5 | 13.2 | 12.1 |
| Control | 2.96 | 3.2 | 3.4 | 3.6 | 4.0 |

EXPERIMENT 4

The suppositories (one 300 mg.) each containing 5 mg. of bleomycin prepared by Examples 19 and 20 or a suppository (containing 5 mg. of bleomycin, one 300 mg, control) prepared by adding bleomycin to a fatty base, Supposire AM (a trade name, made by Gattefose Co. in France) was inserted in the rectum of male Wister rats weighting 200-250 g. fasted for 24 hours just before the experiment and then the anus of each rat was ligated immediately. Then, blood was drawn from the carotid intermittently with a definite time interval and the concentration in plasma of bleomycin was measured by a biological verification method. The results are shown in Table IV.

Table IV

| Test sample | Formulation | * |
|---|---|---|
| Example 19 | Bleomycin | 5.0 mg. |
| (Suppository of | Sodium taurocholate | 9.0 mg. |
| micellar soln.) | 1-Monoolein | 6.0 mg. |
| | Distilled water | 83.3 mg. |
| | Supposire AM | 196.7 mg. |
| Example 20 | Bleomycin | 5.0 mg. |
| (Suppository of | Sodium taurocholate | 8.4 mg. |
| powder) | 1-Monoolein | 5.6 mg. |
| | Supposire AM | 281.0 mg. |
| Control | Bleomycin | 5.6 mg. |
| | Supposire AM | 295.0 mg. |

| | Concentration in plasma (μg./ml.) | | |
|---|---|---|---|
| Test sample | 15 min. | 30 min. | 60 min. |
| Example 19 | 16.46 | 19.05 | 17.50 |
| Example 20 | 17.25 | 16.25 | 16.85 |
| Control | <3.0 | <3.0 | <3.0 |

*Content per one suppository.

EXPERIMENT 5

The lyophilized powder of this invention obtained in Example 1, the micellar solutions of this invention obtained in Examples 22 and 23, or an aqueous solution (control) containing Gentamycin was inserted in the rectum of male rabbits weighting about 2.0 kg. fasted for 24 hours just before the experiment by means of an injector. Then, blood was drawn from the vein of an ear intermittently with a definite time interval and the concentration in plasma of Gentamycin was measured by a biological verification method. The results are shown in Table V.

Table V

| Test sample | Formulation* | |
|---|---|---|
| Example 21 | Gentamycin | 15.0 mg. |
| (Powder) | Sodium taurocholate | 14.9 mg. |
| | 1-Monoolein | 9.9 mg. |
| Example 22 | Gentamycin | 30.0 mg. |
| (Micellar soln.) | Sodium taurocholate | 29.8 mg. |
| | 1-Monoolein | 19.8 mg. |
| Example 23 | Gentamycin | 30.0 mg. |
| (Micellar soln.) | Sodium taurocholate | 14.9 mg. |
| | 1-Monoolein | 9.9 mg. |
| Control | Gentamycin | 30.0 mg. |

| | Concentration in plasma (μg./ml.) | | | | | | |
|---|---|---|---|---|---|---|---|
| Test Sample | 5 min. | 15 min. | 30 min. | 45 min. | 60 min. | 90 min. | 120 min. |
| Example 21 | 8.3 | 9.9 | 12.5 | 12.2 | 10.8 | 8.2 | 7.0 |
| Example 22 | 10.7 | 18.0 | 16.7 | 14.8 | 13.4 | 10.6 | 8.2 |
| Example 23 | 0.9 | 6.3 | 7.5 | 7.6 | 6.3 | 4.9 | 3.8 |
| Control | <0.5 | <0.5 | <0.5 | <0.5 | <0.5 | <0.5 | <0.5 |

*Doses per one rabbit.

EXAMPLE 1

A transparent micellar solution was prepared by adding 1 millimoles of oleic acid to 100 ml. of a phosphoric acid buffer solution (pH 6.5) containing 200 mg. of streptomycin and 490 mg. of sodium glycocholate with stirring by sonification.

EXAMPLE 2

A transparent micellar solution was prepared by adding 1 millimole of fused 1-monoolein to 100 ml. of a phosphoric acid buffer solution (pH 6.5) containing 100 mg. of Gentamycin and 490 mg. of sodium glycocholate with stirring by sonification.

EXAMPLE 3

A transparent micellar solution was prepared by adding 1 millimole of oleic acid to 100 ml. of an aqueous solution containing 76 units of heparin sodium and 540 mg. of sodium taurocholate with stirring by sonification.

EXAMPLE 4

A transparent micellar solution was prepared by adding 1 millimole of fused 1-monoolein to 100 ml. of an aqueous solution containing 76 units of heparin sodium and 540 mg. of sodium taurocholate with stirring by sonification.

EXAMPLE 5

A transparent micellar solution was prepared by adding 1 millimole of oleic acid to 10 100 ml. of an aqueous solution containing 76 units of heparin sodium and 200 mg. of Polysorbate 80 with stirring by sonification.

EXAMPLE 6

To 100 ml. of an aqueous soluton containing 76 units of heparin sodium and 200 mg. of Nikkol HCO-60 was added 1 millimole of oleic acid with stirring by sonification and after dissolving the transparent micellar solution thus formed 1.5 g. of cane sugar, the mixture was lyophilized to provide a powder. In addition, the powder could provide a transparent solution by dispersing it in water.

EXAMPLE 7

A transparent micellar solution was prepared by adding 1 millimole of 1-monoolein to 100 ml. of a phosphoric acid buffer solution (pH 6.5) containing 500 mg. of the sodium salt of benzylpenicillin and 200 mg. of Polysorbate 80 with stirring by sonification.

EXAMPLE 8

A transparent micellar solution was prepared by adding 1 millimole of stearic acid to 100 ml. of an aqueous diluted hydrochloric acid solution (pH 3.0) containing 10,000 unites of insulin and 100 mg. of Nikkol MYS-40 with stirring by sonification.

EXAMPLE 9

To 100 ml. of a phosphoric acid buffer solution (pH 6.5) containing 500 mg. of the sodium salt of cefazolin and 490 mg. of sodium glycocholate was added 1 millimole of fused 1-monolinolein with stirring by sonification and after dissolving 1.5 g. of mannitol in the transparent micellar solution thus obtained, the mixture was lyophilized. Then, 1.5 g. of aliquots of the powder obtained were added to soft capsules for rectal use.

EXAMPLE 10

A transparent micellar solution was prepared by adding 0.5 millimole of oleic acid and 0.5 millimole of 1-monoolein to 100 ml. of a phosphoric acid buffer solution (pH 6.5) containing 300 mg. of bleomycin and 300 mg. of Ryto suga ester P-1570 with stirring by sonification.

EXAMPLE 11

To 100 ml. of a phosphoric acid buffer solution (pH 6.0) containing 500 mg. of the sodium salt of carbenicillin and 1 g. of Pluronic F-68 was added 2 millimoles of 2-butyl-5-methylpentanoic acid with stirring by sonification and after adding 1.0 g. of mannitol to the transparent micellar solution thus obtained to provide a powder. In addition, the powder could provide a transparent solution when it was dispersed in water.

EXAMPLE 12

A transparent micellar solution was prepared by adding 1 millimole of oleic acid to 100 ml. of a phosphoric acid buffer solution (pH 6.5) containing 200 mg. of streptomycin and 540 mg. of sodium taurocholate with stirring by sonification.

EXAMPLE 13

A transparent micellar solution was prepared by adding 1 millimole of linolenic acid to 100 ml. of a phosphoric acid buffer solution (pH 6.5) containing 200 mg. of streptomycin and 540 mg. of sodium taurocholate with stirring by sonification.

EXAMPLE 14

A transparent micellar solution was prepared by adding 1 millimole of lysolecithin to 100 ml. of a phosphoric acid buffer solution (pH 6.5) containing 200 mg. of streptomycin and 540 mg. of sodium taurocholate with stirring by sonification.

EXAMPLE 15

A transparent micellar solution was prepared by adding 1 millimole of 1-monoolein to 100 ml. of a phosphoric acid buffer solution (pH 6.5) containing 200 mg. of streptomycin and 540 mg. of sodium taurocholate with stirring by sonification.

EXAMPLE 16

A transparent micellar solution was prepared by adding 1 millimole of 1-monoolein to 100 ml. of a phosphoric acid buffer solution (pH 6.5) containing 100 mg. of cefazolin and 540 mg. of sodium taurocholate with stirring by sonification.

EXAMPLE 17

A transparent micellar solution was prepared by adding 1 millimole of 1-monoolein to 100 ml. of an aqueous solution containing 250 mg. of bleomycin and 540 mg. of sodium taurocholate with stirring by sonification.

EXAMPLE 18

A transparent micellar solution was prepared by adding 1 millimole of oleic acid to 100 ml. of an aqueous solution containing 250 mg. of bleomycin and 200 mg. of Nikkol HCO-60 with stirring by sonification.

EXAMPLE 19

A transparent micellar solution was prepared by sonificating 10 ml. of an aqueous solution containing 600 mg. of bleomycin, 1.08 g./of sodium taurocholate and 720 mg. of 1-monoolein for 30 seconds. Then, after mixing 1 ml. of the micellar solution with 2.6 g. of a fatty base, Supposire AM fused beforehand at 50° C. followed by sonification for 5 seconds, the mixture was poured in a mold for a suppository and cooled in refrigerator for 60 minutes for 60 minutes to provide. suppositories containing 5 mg. of bleomycin in one suppository (300 mg.).

EXAMPLE 20

A transparent micellar solution was prepared by sonificating 10 ml. of an aqueous solution containing 640 mg. of bleomycin, 1.08 g. of sodium taurocholate, and 120 mg. of 1-monoolein for 30 seconds and 1 ml. of the micellar solution was lyophilized to provide a powder. Then, after mixing the powder with 3.6 g. of a fatty base, Supposire AM fused beforehand at 50° C. followed by sonification for 6 minutes, the mixture was poured in a mold for suppository and cooled in refrigerator for 30 minutes to provide suppositories containing 5 mg. of bleomycin in one suppository (300 mg.).

EXAMPLE 21

A transparent micellar solution was prepared by adding 865 mg. of Gentamycin to 10 ml. of an aqueous solution containing 861 mg. of sodium taurocholate and 571 mg. of 1-monoolein with stirring by sonification. The micellar solution was lyophilized to provide a powder. In addition, the powder could provide a transparent solution when it was dispersed in water.

EXAMPLE 22

A transparent micellar solution was prepared by adding 110 mg. of Gentamycin to 10 ml. of an aqueous solution containing 108 mg. of sodium taurocholate and 72 mg. of 1-monoolein with stirring by sonification.

EXAMPLE 23

A transparent micellar solution was prepared by adding 110 mg. of Gentamycin to 10 ml. of an aqueous solution containing 54 mg. of sodium taurocholate and 36 mg. of 1-monoolein with stirring by sonification.

What is claimed is:

1. A micellar solution composition for rectal use comprising (a) an effective amount of a water-soluble drug which is poorly absorbable on oral administration, (b) 5 to 100 millimoles per liter of at least one of a middle-higher fatty acid and the mono- or di-glyceride thereof, (c) 0.3 to 60g per liter of at least one of a bile acid and a nonionic surface active agent, and (d) water.

2. A powder composition for rectal use prepared by drying a micellar solution comprising (a) an effective amount of a water-soluble drug which is poorly absorbable at oral administration, (b) 5 to 100 millimoles per liter of at least one of a middle-higher fatty acid and the mono- or di-glyceride thereof, (c) 0.3 to 60g per liter of at least one of a bile acid and a nonionic surface active agent, and (d) water.

3. The micellar solution composition for rectal use as claimed in claim 1 wherein said water-soluble drug which is poorly absorbable on oral use is a member selected from the group consisting of streptomycin, Gentamycin, cefaxolin, bleomycin and heparin.

4. The powder composition for rectal use as claimed in claim 2 wherein said water-soluble drug which is poorly absorbable on oral administration is a member selected from the group consisting of streptomycin, Gentamycin, cefazolin, bleomycin, and heparin.

5. The micellar solution composition for rectal use as claimed in claim 1 wherein said middle-higher fatty acid and the mono- or di-glyceride thereof is a member selected from the group consisting of oleic acid, linoleic acid, 1-monoolein, or lysolecithin.

6. The powder composition for rectal use as claimed in claim 2 wherein said one middle-higher fatty acid and the mono- or di-glyceride thereof is a member selected from the group consisting of oleic acid, linoleic acid, 1-monoolein, and /ysolecithin.

7. The micellar solution composition for rectal use as claimed in claim 1 wherein said bile acid is sodium glycocholate or sodium taurocholate.

8. The powder composition for rectal use as claimed in claim 2 wherein said bile acid is sodium glycocholate or sodium taurocholate.

9. The micellar solution composition for rectal use as claimed in claim 1 wherein said nonionic surface active agent is a polyoxyethylene sorbitan fatty acid ester or a polyoxyethylene hardened castor oil derivative.

10. The powder composition for rectal use as claimed in claim 2 wherein said nonionic surface active agent is a polyoxyethylene sorbitan fatty acid ester or a polyoxyethylene hardened castor oil derivative.

11. The powder composition as claimed in claim 2, further including a pharmaceutically acceptable carrier.

12. A method of administering a water-soluble drug which is poorly absorbable on oral administration comprising rectally administering an effective amount of the composition of claim 1.

13. A method of administering a water-soluble drug which is poorly absorbable on oral administration comprising rectally administering an effective amount of the composition of claim 2.

* * * * *

UNITED STATES PATENT AND TRADEMARK OFFICE
CERTIFICATE OF CORRECTION

PATENT NO. : 4,156,719
DATED : May 29, 1979
INVENTOR(S) : Hitoshi Sezaki, et al

It is certified that error appears in the above—identified patent and that said Letters Patent is hereby corrected as shown below:

Column 2, line 15: "of the" should be --to the--.

Column 3, line 18: "lypolecithin" should be --lysolecithin--.

Column 8, line 40: "unites" should be --units--.

Column 10, line 65: "/ysolecithin" should be --lysolecithin--.

Signed and Sealed this

First Day of April 1980

[SEAL]

Attest:

SIDNEY A. DIAMOND

Attesting Officer

Commissioner of Patents and Trademarks